US007989620B2

(12) United States Patent
Gabos et al.

(10) Patent No.: US 7,989,620 B2
(45) Date of Patent: Aug. 2, 2011

(54) HYDANTOIN DERIVATIVES FOR THE TREATMENT OF OBSTRUCTIVE AIRWAY DISEASES

(75) Inventors: Balint Gabos, Lund (SE); Lena Ripa, Lund (SE); Kristina Stenvall, Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/629,630

(22) Filed: Dec. 2, 2009

(65) Prior Publication Data

US 2010/0144771 A1    Jun. 10, 2010

Related U.S. Application Data

(63) Continuation of application No. 11/571,637, filed as application No. PCT/SE2005/001092 on Jul. 4, 2005, now Pat. No. 7,648,992.

(30) Foreign Application Priority Data

Jul. 5, 2004    (SE) ...................................... 0401762

(51) Int. Cl.
   *C07D 401/14*    (2006.01)
   *C07D 403/14*    (2006.01)
   *A61K 31/506*    (2006.01)
   *A61P 19/02*    (2006.01)

(52) U.S. Cl. ........ 544/316; 544/333; 544/242; 514/256; 514/269; 514/275

(58) Field of Classification Search .................. 544/316, 544/333, 242; 514/269, 256, 275
See application file for complete search history.

(56) References Cited

U.S. PATENT DOCUMENTS

| | | | |
|---|---|---|---|
| 2,327,890 A | 8/1943 | Henze | |
| 2,745,875 A | 5/1956 | Ehrhart et al. | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 4,983,771 A | 1/1991 | Bryker et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,919,790 A | 7/1999 | Allen et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,291,685 B1 | 9/2001 | Junghans et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B2 | 5/2005 | Sheppeck et al. | |
| 6,906,053 B2 | 6/2005 | Sheppeck et al. | |
| 7,078,424 B2 | 7/2006 | Hamilton et al. | |
| 7,132,434 B2 | 11/2006 | Eriksson et al. | |
| 7,354,940 B2 | 4/2008 | Henriksson et al. | |
| 7,368,465 B2 | 5/2008 | Eriksson et al. | |
| 7,427,631 B2* | 9/2008 | Eriksson et al. ............. 514/318 |
| 7,625,934 B2 | 12/2009 | Eriksson et al. | |
| 7,648,992 B2* | 1/2010 | Gabos et al. .................. 514/256 |
| 7,655,664 B2 | 2/2010 | Gabos et al. | |
| 7,662,845 B2 | 2/2010 | Henriksson et al. | |
| 7,666,892 B2 | 2/2010 | Eriksson et al. | |
| 7,700,604 B2 | 4/2010 | Gabos et al. | |
| 7,754,750 B2 | 7/2010 | Eriksson et al. | |
| 7,772,403 B2 | 8/2010 | Cornwall et al. | |
| 2002/0006920 A1 | 1/2002 | Robinson et al. | |

(Continued)

FOREIGN PATENT DOCUMENTS

EP    0175312    3/1986

(Continued)

OTHER PUBLICATIONS

Demedts, et al., Thorax 2006;61:196-201.*
Kelly, et al., Current Opinion in Pulmonary Medicine. 9(1):28-33, Jan. 2003.*
Dorman, et al., Recent Patents on Cardiovascular Drug Discovery, 2007, 2, 000-000.*
Murphy, et al., Nature Clin. Practice Rheumatology (2008)4, 128-135.*
Johnson, et al., PNAS, Oct. 25, 2005 vol. 102 No. 43 15575-15580.*
Borkakoti, Biochemical Society Transactions (2004) vol. 32, part 1, 17-20.*

(Continued)

*Primary Examiner* — Venkataraman Balasubramanian
(74) *Attorney, Agent, or Firm* — Fish & Richardson P.C.

(57) ABSTRACT

The invention provides compounds of formula (I), wherein $R^1$ and $R^2$ are as defined in the specification; processes for their preparation; pharmaceutical compositions containing them; a process for preparing the pharmaceutical compositions; and their use in therapy.

2 Claims, No Drawings

U.S. PATENT DOCUMENTS

| | | | |
|---|---|---|---|
| 2002/0028835 | A1 | 3/2002 | Hu et al. |
| 2002/0065219 | A1 | 5/2002 | Naidu et al. |
| 2002/0091107 | A1 | 7/2002 | Madar et al. |
| 2003/0130273 | A1 | 7/2003 | Sheppeck et al. |
| 2004/0044215 | A1 | 3/2004 | Alcade et al. |
| 2004/0106659 | A1 | 6/2004 | Af Rosenschold |
| 2004/0110809 | A1 | 6/2004 | Lepisto et al. |
| 2004/0116486 | A1 | 6/2004 | Lepisto et al. |
| 2004/0127528 | A1 | 7/2004 | Eriksson et al. |
| 2004/0138276 | A1 | 7/2004 | Eriksson et al. |
| 2004/0147573 | A1 | 7/2004 | Eriksson et al. |
| 2004/0152697 | A1 | 8/2004 | Chan et al. |
| 2004/0209874 | A1 | 10/2004 | Sheppeck et al. |
| 2004/0266832 | A1 | 12/2004 | Li et al. |
| 2005/0019994 | A1 | 1/2005 | Chang |
| 2005/0026990 | A1 | 2/2005 | Eriksson et al. |
| 2005/0171096 | A1 | 8/2005 | Sheppeck et al. |
| 2005/0245586 | A1 | 11/2005 | Henriksson et al. |
| 2005/0256176 | A1 | 11/2005 | Burrows et al. |
| 2006/0019994 | A1 | 1/2006 | Burrows et al. |
| 2006/0063818 | A1 | 3/2006 | Burrows et al. |
| 2006/0276524 | A1 | 12/2006 | Henriksson et al. |
| 2008/0004317 | A1 | 1/2008 | Gabos et al. |
| 2008/0032997 | A1 | 2/2008 | Gabos et al. |
| 2008/0064710 | A1 | 3/2008 | Gabos et al. |
| 2008/0171882 | A1 | 7/2008 | Eriksson et al. |
| 2008/0221139 | A1 | 9/2008 | Chapman et al. |
| 2008/0262045 | A1 | 10/2008 | Eriksson et al. |
| 2008/0293743 | A1 | 11/2008 | Gabos et al. |
| 2008/0306065 | A1 | 12/2008 | Eriksson et al. |
| 2009/0054659 | A1 | 2/2009 | Cornwall et al. |
| 2009/0221640 | A1 | 9/2009 | Briggner et al. |
| 2010/0144771 | A1 | 6/2010 | Gabos et al. |
| 2010/0256166 | A1 | 10/2010 | Gabos et al. |

FOREIGN PATENT DOCUMENTS

| | | |
|---|---|---|
| EP | 0212617 | 3/1987 |
| EP | 0255390 | 2/1988 |
| EP | 0442584 | 8/1991 |
| EP | 0486280 | 5/1992 |
| EP | 0580210 | 1/1994 |
| EP | 0640594 | 3/1995 |
| EP | 0709375 | 5/1996 |
| EP | 1397137 | 11/1996 |
| EP | 0909754 | 4/1999 |
| EP | 1117616 | 7/2001 |
| EP | 1149843 | 10/2001 |
| EP | 1191024 | 3/2002 |
| EP | 1550725 | 7/2005 |
| WO | WO 92/01062 | 1/1992 |
| WO | WO 95/14025 | 5/1995 |
| WO | WO 96/21640 | 7/1996 |
| WO | WO 96/27583 | 9/1996 |
| WO | WO 98/50359 | 11/1998 |
| WO | WO 99/06361 | 2/1999 |
| WO | WO 99/24399 | 5/1999 |
| WO | WO 99/42443 | 8/1999 |
| WO | WO 99/62880 | 12/1999 |
| WO | WO 00/09103 | 2/2000 |
| WO | WO 00/12477 | 3/2000 |
| WO | WO 00/12478 | 3/2000 |
| WO | WO 00/35886 | 6/2000 |
| WO | WO 00/40577 | 7/2000 |
| WO | WO 00/44770 | 8/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/06232 | 1/2002 |
| WO | WO 02/14262 | 2/2002 |
| WO | WO 02/14354 | 2/2002 |
| WO | WO 02/20515 | 3/2002 |
| WO | WO 02/074748 | 9/2002 |
| WO | WO 02/074749 | 9/2002 |
| WO | WO 02/074750 | 9/2002 |
| WO | WO 02/074751 | 9/2002 |
| WO | WO 02/074752 | 9/2002 |
| WO | WO 02074767 A1 * | 9/2002 |
| WO | WO 02/096426 | 12/2002 |
| WO | WO 03/040098 | 5/2003 |
| WO | WO 03/087057 | 10/2003 |
| WO | WO 03/093260 | 11/2003 |
| WO | WO 03/094919 | 11/2003 |
| WO | WO 2004/020415 | 3/2004 |
| WO | WO 2004/024060 | 3/2004 |
| WO | WO 2004/024698 | 3/2004 |
| WO | WO 2004/024715 | 3/2004 |
| WO | WO 2004/024718 | 3/2004 |
| WO | WO 2004/024721 | 3/2004 |
| WO | WO 2004/033632 | 4/2004 |
| WO | WO 2004/108086 | 12/2004 |
| WO | WO 2006/004532 | 1/2006 |
| WO | WO 2006/004533 | 1/2006 |
| WO | WO 2006/065215 | 6/2006 |
| WO | WO 2006/065216 | 6/2006 |
| WO | WO 2006/077387 | 7/2006 |
| WO | WO 2007/106021 | 9/2007 |
| WO | WO 2007/106022 | 9/2007 |

OTHER PUBLICATIONS

Aharony et al. "Pharmacological Characterization of a New Class of Nonpeptide Neurokinin A Antagonists that Demonstrate Species Selectivity." J. Pharmacol. Exp. Ther. 274:3 (1995), pp. 1216-1221.

Aigner et al., "Growth Plate Cartilage as Developmental Model in Osteoarthritis Research—Potentials and Limitations", Current Drug Targets 8(2):377-385 (2007).

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-5143, 1981.

Avgeropoulos et al., "New Treatment Strategies for Malignant Gliomas", The Oncologist 4:209-224 (1999).

Banfield et al., "Heterocyclic Derivatives of Guanidine. Part V. Reaction of Some Glycidic Esters with Guanidines", The Journal of the Chemical Society 511:2747-2756 (1963).

Belvisi et al., "The role of matrix metalloproteinases (MMPs) in the patho-physiology of chronic obstructive pulmonary disease (COPD): a therapeutic role for inhibitors of MMPs?", Inflammation Research 52:95-100 (2003).

Borchers et al., "Acrolein-Induced MUC5ac Expression in Rat Airways", The American Physiological Society 274:L573-L581 (1998).

Bright et al. "Monoclonal Antibodies as Surrogate Receptors in High Throughput Screen for Compounds that Enhance Insulin Sensitivity." Life Sciences. 61:23 (1997), pp. 2305-2315.

Bruce et al., "The effect of marimastat, a metalloprotease inhibitor, on allergen-induced asthmatic hyper-activity", Toxicol & Appl. Pharmacol. 205:126-132 (2005).

Carmeliet, "Proteinases in Cardiovascular Aneurysms and Rupture: Targets for Therapy?", The Journal of Clinical Investigation 105(11):1519-1520 (2000).

Catterall et al., "Drugs in development: bisphosphonates and metalloproteinase inhibitors", Arthritis Res Ther 5:12-24 (2003).

Chambers et al., "Changing Views of the Role of Matrix Metalloproteinases in Metastasis", J Natl Cancer Inst 89:1260-1270 (1997).

Chemical Abstracts, vol. 65, 1966, Abstract No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Chodosh et al., "Comparative trials of doxycycline versus amoxicillin, cephalexin and enoxacin in bacterial infections in chronic bronchitis and asthma", Scand. J Infect. Dis. Suppl. 53:22-8 (1988).

Comber et al., "5,5-Disubstituted Hydantoins: Syntheses and Anti-HIV Activity", J Med. Chem. 35:3567-3572 (1992).

COPD; http://www.lungsonline.com/copd.html, downloaded Aug. 22, 2008.

Croce, P. et al. "Stereoselective aldol addition of a chirai glycine enloate synthon to heteroaromatic aldehydes." Heterocycles, 52:3 (2000) pp. 1337-1344.

Dahan et al., "Expression of Matrix Metalloproteinases in Healthy and Diseased Human Gingiva", *Journal of Clinical Periodontology* 28:128-136 (2001).

Doherty et al., "Therapeutic Developments in Matrix Metalloproteinase Inhibition", *Expert Opinion Ther. Patents* 12(5):665-707 (2002).

Dorwald, F.Z., "Side Reactions in Organic Synthesis: A Guide to Successful Synthesis Design", 2005, Wiley-VCH Verlag GmbH & Co. KGaA, Weinheim.

Doxycycline hyclate; http://en.wikipedia.org/wiki/Doxycycline_hyclate, downloaded Aug. 22, 2008.

Elliot et al., "The Clinical Potential of Matrix Metalloproteinase Inhibitors in the Rheumatic Disorders", *Drugs & Aging* 18(2):87-99 (2001).

Fujita et al., "The pathogenesis of COPD: Lessons Learned from in vivo Animal Models", *Med. Sci Monit.* 13(2):RA19-24 (2007).

Gramatica et al., STN International, HCAPLUS Database, Columbus, OH, Accession No. 2002:356947, Reg. No. 36734-19-7.

Hautamaki et al., "Requirement for Macrophage Elastase for Cigarette Smoke-Induced Emphysema in Mice", *Science* 277:2002-2004 (2002).

Hirrlinger et al., "Purification and properties of an amidase from *Rhodococcus erythropolis* MP50 which enantioselectively hydrolyzes 2-arylpropionamides", *J. Bacteriology* 178(12):3501-3507 (1996).

Knabe, J. "Razemate und enantiomere basisch substituierter 5-phenylhydantoine." Pharmazie. 52:12 (1997) pp. 912-919.

Lindy et al., "Matrix Metalloproteinase 13 (Collagenase 3) in Human Rheumatoid Synovium Arthritis Rheumatism," *Arthritis and Rheumatism* 40(8):1391-1399 (1997).

Lora-Tamayo et al. "Anticancerousos Potenciales." An. Quim. 64:6 (1968), pp. 591-606.

MacFadyen, "Can Matrix Metalloproteinase Inhibitors Provide a Realistic Therapy in Cardiovascular Medicine", *Current Opinion in Pharmacology* 7:171-178 (2007).

Mandal, Malay et al., "*Clinical Implications of Matrix Metalloproteinases*", Molecular and Cellular Biochemistry, 252:305-329, (2003).

Michaelides et al., "Recent Advances in Matrix Metalloproteinase Inhibitors Research", *Current Pharmaceutical Design* 5:787-819 (1999).

Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.

Mock et al., "Principles of Hydroxamate Inhibition of Metalloproteases: Carboxypeptidase A", *Biochemistry* 39:13945-13952 (2000).

Morris et al., PubMed Abstract, "Sequential steps in hematogenous metastasis of cancer cells studied by in vivo videomicroscopy", *Invasion Metastasis* 17:281-296 (1997).

Nakajima, Riichiro et al. "The utility of 4-(2-thienyl)pyridines as a derivatization reagent for hplc and ce." Analytical Sciences. 7, Supplement 1991, pp. 177-180.

Nicolet, Ben. "Interpretation of the Dyhydration of Acetylglutamic acid by Means of Glutamylthiohydantoin Derivatives." Journal of the American Chemical Society, 1930, pp. 1192-1195.

Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.

Peng, Sean X. "Separation and identification of methods for metalloproteinase inhibitors." Journal of Chromatography B. 764 (2001), pp. 59-80.

PubMed Abstract for: Rifkin, B.R. et al, "Blocking Periodontal Disease Progression by Inhibiting Tissue-Destructive Enzymes: A Potential Therapeutic Role for Tetracyclines and Their Chemically-Modified Analogs", Periodontol, Aug. 1993 64 (8 Suppl), pp. 819-827 (see Rifkin below).

Pyo et al., "Targeted gene disruption of matrix metalloproteinase-9 (gelatinase B) suppresses development of experimental abdominal aortic aneurysms", *J. Clinical Investigation* 105:1641-1649 (2000).

Rasmussen et al., "Matrix Metalloproteinase Inhibition as a Novel Anticancer Strategy: A Review with Special Focus on Batimastat and Marimastat", *Pharmacol. Ther.* 75:69-75 (1997).

Reisner, "Some α-amino acids containing a sulfonamide group", *J. Am. Chem. Soc.* 78:5102-5104 (1956). CAS abstract and search structure only.

Rifkin et al, "Blocking Periodontal Disease Progression by Inhibiting Tissue-Destructive Enzymes: A Potential Therapeutic Role for Tetracyclines and Their Chemically-Modified Analogs", Periodontol Aug. 1993 64 (8 Suppl), pp. 819-827.

Rouis et al., "Adenovirus-mediated overexpression of tissue inhibitor of metalloproteinase-1 reduces atherosclerotic lesions in apolipoprotein E-deficient mice", *Circulation* 100:533-540 (1999).

Saito, Sei-ichi et al. "A new synthesis of deglyco-bleomycine A2 aiming at the total synthesis of bleomycin." Tetrahedron Letters. 23(5) (1982), pp. 529-532.

Simone, "Oncology: Introduction", Cecil Textbook of Medicine, 20th Edition, vol. 1, pp. 1004-1010 (1996).

Smith, Michael B., Organic Synthesis Second Edition, 3.9.A Oxidation of sulfur compounds, McGraw-Hill 2002, ISBN-0-07-048242-X, p. 280.

STN International, file CAPLUS, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.

STN International, file CAPLUS, accession No. 1994:299315, Document No. 120:299315, Sakamoto, Shuichi et al., "Preparation of pyridylserine derivatives as psychotropics," WO, A1, 9320053, 19931014, See CAS RN 154696-31-8, 154697-48-0.

STN International, file CAPLUS, accession No. 1997:644516, Batty, Craig et al. "Synthesis and exchange reaction of 5-alkyl-2oxo-6-thioxo-1,2,3,6-hexahydropyrimidine-4-carboxylic acids" & Journal of Heterocyclic Chemistry (1997), 34:3, 1355-1367.

STN International, file CAPLUS, accession No. 2002:640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.

STN International, File CAPLUS, CAPLUS accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606.

STN International, File CAPLUS, CAPLUS accession No. 1974:463633, Doc. No. 81:63633, Blaha, Ludvik et al.: "5-Methyl-5-phenoxymethyl-hydantoins", & CS 151744, B, 19731119.

STN International, File CAPLUS, CAPLUS accession No. 1988:631020, Doc. No. 109:231020, Mitsui Toatsu Chemicals, Inc.: "Process for the preparation of 5-benzylhydantoins as intermediates for aromatic amino acids": & JP, A2, 63079879, 19880409.

STN International, File CAPLUS, CAPLUS accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.

STN International, File CAPLUS, CAPLUS accession No. 1990:138955, Doc. No. 112:138955, Crooks, Peter A. et al.: "Synthesis of 5-benzoyl-5-phenyl-and-5-(Phenylhydroxymethyl)-5-phenylhydantoins as potential anticonvulsants"; & J. Heterocycl. Chem. (1989), 26(4), 1113-17.

Visse et al., "Matrix Metalloproteinases and Tissue Inhibitors of Metalloproteinases", *Circ Res.* 92:827-839 (2003).

Wernicke, Dirk et al., "Cloning of Collagenase 3 from the Synovial Membrane and Its Expression in Rheumatoid Arthritis and Osteoarthritis", *The Journal of Rheumatology*, 23:590-595, (1996).

Whittaker, Mark et al., "Design and Therapeutic Application of Matrix Metalloproteinase Inhibitors", *Chemical Reviews*, 99:2735-2776, (1999).

Wikipedia, Matrix metalloproteinase, updated Mar. 9, 2009, <http://en.wikipedia.org/wiki/Matrix_metalloproteinase>, downloaded Mar. 11, 2009.

Wikipedia, Minocycline, updated Feb. 28, 2009, http://en.wikipedia.org/wiki/Minocycline, downloaded Mar. 11, 2009.

Wingerchuk, Dean M. et al., "Multiple Sclerosis: Current Pathophysiological Concepts", Biology of Disease, Lab Invest 2001, vol. 81, pp. 263-281.

* cited by examiner

HYDANTOIN DERIVATIVES FOR THE TREATMENT OF OBSTRUCTIVE AIRWAY DISEASES

CROSS-REFERENCE TO RELATED APPLICATIONS

This application is a continuation of U.S. application Ser. No. 11/571,637, filed on Jan. 4, 2007 (now U.S. Pat. No. 7,648,992), which is the United States National Stage of International Application No. PCT/SE2005/001092, filed Jul. 4, 2005, which claims the benefit of Swedish Application Serial No. 0401762-0, filed Jul. 5, 2004; each of these prior applications is incorporated herein by reference in its entirety.

The present invention relates to novel hydantoin derivatives, processes for their preparation, pharmaceutical compositions containing them and their use in therapy.

Metalloproteinases are a superfamily of proteinases (enzymes) whose numbers in recent years have increased dramatically. Based on structural and functional considerations these enzymes have been classified into families and subfamilies as described in N. M. Hooper to (1994) FEBS Letters 354:1-6. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP11), matrilysin (MMP7), metalloelastase (MMP 12), enamelysin (MMP 19), the MT-MMPs (MMP 14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem. J. 321:265-279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atheroscelerosis; asthma; rhinitis; and chronic obstructive pulmonary diseases (COPD).

MMP 12, also known as macrophage elastase or metalloelastase, was initially cloned in the mouse by Shapiro et al [1992, Journal of Biological Chemistry 267: 4664] and in man by the same group in 1995. MMP 12 is preferentially expressed in activated macrophages, and has been shown to be secreted from alveolar macrophages from smokers [Shapiro et al, 1993, Journal of Biological Chemistry, 268: 23824] as well as in foam cells in atherosclerotic lesions [Matsumoto et al, 1998, Am. J. Pathol. 153: 109]. A mouse model of COPD is based on challenge of mice with cigarette smoke for six months, two cigarettes a day six days a week. Wild-type mice developed pulmonary emphysema after this treatment. When MMP12 knock-out mice were tested in this model they developed no significant emphysema, strongly indicating that MMP 12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29-38. It was recently discovered that smoking increases macrophage infiltration and macrophage-derived MMP-12 expression in human carotid artery plaques Kangavari [Matetzky S, Fishbein M C et al., Circulation 102:(18), 36-39 Suppl. S, Oct. 31, 2000].

MMP9 (Gelatinase B; 92 kDa TypeIV Collagenase; 92 kDa Gelatinase) is a secreted protein which was first purified, then cloned and sequenced, in 1989 [S. M. Wilhelm et al (1989) J. Biol. Chem. 264 (29): 17213-17221; published erratum in J. Biol. Chem. (1990) 265 (36): 22570]. A recent review of MMP9 provides an excellent source for detailed information and references on this protease: T. H. Vu & Z. Werb (1998) (In: Matrix Metalloproteinases, 1998, edited by W. C. Parks & R. P. Mecham, pp. 115-148, Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, the expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases -1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues.

MMP9 release, measured using enzyme immunoassay, was significantly enhanced in fluids and in AM supernatants from untreated asthmatics compared with those from other populations [Am. J. Resp. Cell & Mol. Biol., November 1997, 17 (5):583-591]. Also, increased MMP9 expression has been observed in certain other pathological conditions, thereby implicating MMP9 in disease processes such as COPD, arthritis, tumour metastasis, Alzheimer's disease, multiple sclerosis, and plaque rupture in atherosclerosis leading to acute coronary conditions such as myocardial infarction.

A number of metalloproteinase inhibitors are known (see for example the reviews of MMP inhibitors by Beckett R. P. and Whittaker M., 1998, Exp. Opin. Ther. Patents, 8(3):259-282, and by Whittaker M. et al, 1999, Chemical Reviews 99(9):2735-2776).

WO 02/074767 discloses hydantoin derivatives of formula

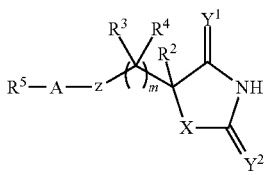

that are useful as MMP inhibitors, particularly as potent MMP12 inhibitors. The following three compounds are specifically disclosed in WO 02/074767

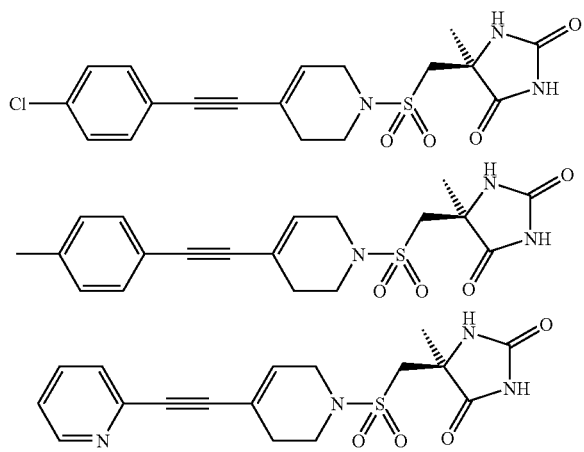

We have now discovered a group of compounds that are inhibitors of metalloproteinases and are of particular interest in inhibiting MMPs such as MMP12 and MMP9. The compounds of the present invention have beneficial potency, selectivity and/or pharmacokinetic properties. The compounds of the present invention are within the generic scope of WO 02/074767 but are of a type not specifically exemplified therein.

In accordance with the present invention, there is therefore provided a compound of formula (I)

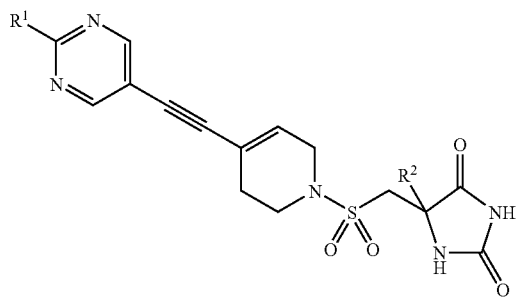

wherein $R^1$ represents C1 to 2 alkyl, cyclopropyl, $OCH_3$, $SCH_3$ or $OCF_3$; said alkyl or cyclopropyl group being optionally further substituted by one or more fluoro atoms; and $R^2$ represents C1 to 3 alkyl; and pharmaceutically acceptable salts thereof.

The compounds of formula (I) may exist in enantiomeric forms. It is to be understood that all enantiomers, diastereomers, racemates and mixtures thereof are included within the scope of the invention.

Compounds of formula (I) may also exist in various tautomeric forms. All possible tautomeric forms and mixtures thereof are included within the scope of the invention.

In one embodiment, $R^1$ represents C1 to 2 alkyl or cyclopropyl; said alkyl or cyclopropyl group being optionally further substituted by one or more fluoro atoms.

In another embodiment, $R^1$ represents C1 to 2 alkyl optionally further substituted by one or more fluoro atoms.

In one embodiment, $R^1$ represents cyclopropyl optionally further substituted by one or more fluoro atoms.

In one embodiment, $R^1$ represents cyclopropyl.

In one embodiment, $R^1$ represents trifluoromethyl.

In one embodiment, $R^1$ represents $OCH_3$ or $SCH_3$.

In one embodiment, $R^2$ represents methyl or ethyl. In one embodiment, $R^2$ represents methyl.

In one embodiment, $R^1$ represents C1 to 2 alkyl or cyclopropyl; said alkyl or cyclopropyl group being optionally further substituted by one or more fluoro atoms and $R^2$ represents methyl or ethyl.

In one embodiment, $R^1$ represents C1 to 2 alkyl or cyclopropyl; said alkyl or cyclopropyl group being optionally further substituted by one or more fluoro atoms and $R^2$ represents methyl.

In one embodiment, $R^1$ represents C1 to 2 alkyl optionally further substituted by one or more fluoro atoms and $R^2$ represents methyl or ethyl.

In one embodiment, $R^1$ represents $CF_3$ and $R^2$ represents methyl or ethyl.

In one embodiment, $R^1$ represents cyclopropyl and $R^2$ represents methyl or ethyl.

Unless otherwise indicated, the term "C1 to 3 alkyl" referred to herein denotes a straight or branched chain alkyl group having from 1 to 3 carbon atoms. Examples of such groups include methyl, ethyl, n-propyl and i-propyl. The term "C1 to 2 alkyl" denotes methyl or ethyl.

Examples of a C1 to 2 alkyl optionally further substituted by one or more fluoro atoms include $CF_3$, $CH_2F$, $CH_2CF_3$, $CF_2CH_3$ and $CF_2CF_3$.

Examples of a cyclopropyl ring optionally further substituted by one or more fluoro atoms include 1-fluoro-1-cyclo propyl, 2,2-difluoro-l-cyclopropyl and 2,3-difluoro-1-cyclopropyl:

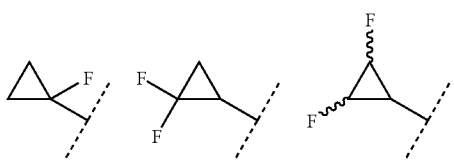

Examples of compounds of the invention include:
(5S)-5-({[4-[(2-cyclopropylpyrimidin-5-yl)ethynyl]-3,6-dihydropyridin-1(2H)-yl]sulfonyl}methyl)-5-methylimidazolidine-2,4-dione;
(5S)-5-methyl-5-({[4-{[2-(methylthio)pyrimidin-5-yl]ethynyl}-3,6-dihydropyridin-1(2H)-yl]sulfonyl}methyl)imidazolidine-2,4-dione;
(5S)-5-methyl-5-({[4-{[2-(trifluoromethyl)pyrimidin-5-yl]ethynyl}-3,6-dihydropyridin-1(2H)-yl]sulfonyl}methyl)imidazolidine-2,4-dione;
(5S)-5-methyl-5-({[4-[(2-methylpyrimidin-5-yl)ethynyl]-3,6-dihydropyridin-1(2H)-yl]sulfonyl}methyl)imidazolidine-2,4-dione;
(5S)-5-({[4-[(2-ethylpyrimidin-5-yl)ethynyl]-3,6-dihydropyridin-1(2H)-yl]sulfonyl}methyl)-5-methylimidazolidine-2,4-dione;
(5S)-5-({[4-[(2-methoxypyrimidin-5-yl)ethynyl]-3,6-dihydropyridin-1(2H)-yl]sulfonyl}methyl)-5-methylimidazolidine-2,4-dione;
and pharmaceutically acceptable salts thereof.

Each exemplified compound represents a particular and independent aspect of the invention.

The compounds of formula (I) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

Where optically isomers exist in the compounds of the invention, we disclose all individual optically active forms and combinations of these as individual specific embodiments of the invention, as well as their corresponding racemates.

Preferably the compounds of formula (I) have (5S)-stereochemistry as shown below:

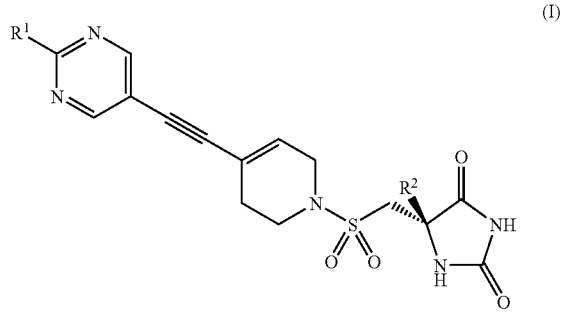

(I)

Where tautomers exist in the compounds of the invention, we disclose all individual tautomeric forms and combinations of these as individual specific embodiments of the invention.

The present invention includes compounds of formula (I) in the form of salts. Suitable salts include those formed with organic or inorganic acids or organic or inorganic bases. Such salts will normally be pharmaceutically acceptable salts although non-pharmaceutically to acceptable salts may be of utility in the preparation and purification of particular compounds. Such salts include acid addition salts such as hydrochloride, hydrobromide, citrate, tosylate and maleate salts and salts formed with phosphoric acid or sulphuric acid. In another aspect suitable salts are base salts such as an alkali metal salt, for example, sodium or potassium, an alkaline earth metal salt, for example, calcium or magnesium, or an organic amine salt, for example, triethylamine.

Salts of compounds of formula (I) may be formed by reacting the free base or another salt thereof with one or more equivalents of an appropriate acid or base.

The compounds of formula (I) are useful because they possess pharmacological acivity in animals and are thus potentially useful as pharmaceuticals. In particular, the compounds of the invention are metalloproteinase inhibitors and may thus be used in the treatment of diseases or conditions mediated by MMP12 and/or MMP9 such as asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), and hematological disorders.

In general, the compounds of the present invention are potent inhibitors of MMP9 and MMP 12. The compounds of the present invention also show good selectivity with respect to a relative lack of inhibition of various other MMPs such as MMP8, MMP14 and MMP19. In addition, the compounds of the present invention also, in general, have improved log D values, in particular, having log D values in the range of 0.5<log D<2.0. Log D is a parameter that reflects the lipophilicity of a compound at physiological pH. As a consequence of these favourable log D values, the compounds of the present invention possess improved solubility characteristics and reduced plasma protein binding, leading to improved pharmacokinetic and pharmacodynamic properties.

Accordingly, the present invention provides a compound of formula (I), or a pharmaceutically acceptable salt thereof, as hereinbefore defined for use in therapy.

In another aspect, the invention provides the use of a compound of formula (I), or a pharmaceutically acceptable salt thereof, as hereinbefore defined in the manufacture of a medicament for use in therapy.

In another aspect, the invention provides the use of a compound of formula (I), or a pharmaceutically acceptable salt thereof, as hereinbefore defined in the manufacture of a medicament for use in the treatment of diseases or conditions in which inhibition of MMP12 and/or MMP9 is beneficial.

In another aspect, the invention provides the use of a compound of formula (I), or a pharmaceutically acceptable salt thereof, as hereinbefore defined in the manufacture of a medicament for use in the treatment of inflammatory disease.

In another aspect, the invention provides the use of a compound of formula (I), or a pharmaceutically acceptable salt thereof, as hereinbefore defined in the manufacture of a medicament for use in the treatment of an obstructive airways disease such as asthma or COPD.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of treating a disease or condition in which inhibition of MMP12 and/or MMP9 is beneficial which comprises administering to a patient a therapeutically effective amount of a compound of formula (I) or a pharmaceutically acceptable salt thereof as hereinbefore defined.

The invention also provides a method of treating an obstructive airways disease, for example, asthma or COPD, which comprises administering to a patient a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder to be treated. The daily dosage of the compound of formula (I)/salt (active ingredient) may be in the range from 0.001 mg/kg to 75 mg/kg, in particular from 0.5 mg/kg to 30 mg/kg. This daily dose may be given in divided doses as necessary.

Typically unit dosage forms will contain about 1 mg to 500 mg of a compound of this invention.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition. Conventional procedures for the selection and preparation of suitable pharmaceutical formulations are described in, for example, "Pharmaceuticals—The Science of Dosage Form Designs", M. E. Aulton, Churchill Livingstone, 1988.

Thus, the present invention also provides a pharmaceutical composition comprising a compound of formula (I) or a pharmaceutically acceptable salt thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions of this invention may be administered in a standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove such as "Symbicort" (trade mark) product.

The present invention further provides a process for the preparation of a compound of formula (I) or a pharmaceutically acceptable salt thereof as defined above which, comprises:

a) reaction of a compound of formula (II)

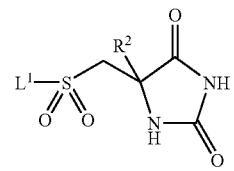

(II)

wherein $R^2$ is as defined in formula (I) and $L^1$ represents a leaving group, with a compound of formula (III) (or a salt thereof)

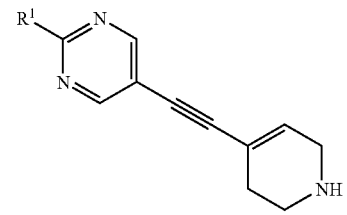

(III)

wherein $R^1$ is as defined in formula (I); or b) reaction of a compound of formula (X)

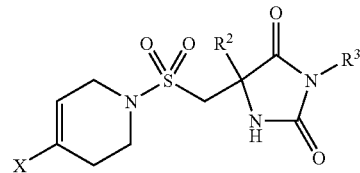

(X)

where $R^2$ is as defined in formula (I), $R^3$ is H or a suitable protecting group and X is a leaving group such as halide or triflate; with an acetylenic compound of formula (IX)

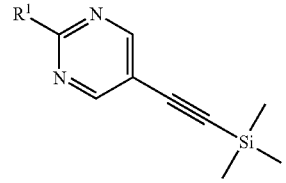

(IX)

wherein $R^1$ is as defined in formula (I); or c) reaction of a compound of formula (XI)

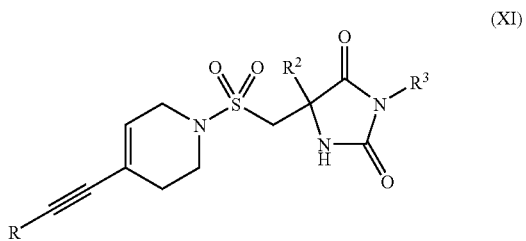

wherein R represents H or trimethylsilyl, R² is as defined in formula (I) and R³ represents H or a suitable protecting group; with an aryl halide or triflate of formula (VI)

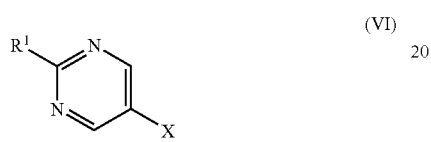

wherein R¹ is as defined in formula (I) and X represents halide or triflate; and optionally thereafter forming a pharmaceutically acceptable salt thereof In the above process (a), suitable leaving groups L¹ include halo, particularly chloro. The reaction is preferably performed in a suitable solvent optionally in the presence of an added base for a suitable period of time, typically 0.5 to 24 h, at ambient to reflux temperature. Typically solvents such as pyridine, dimethylformamide, tetrahydrofuran, acetonitrile or dichloromethane are used. When used, the added base may be an organic base such as triethylamine, diisopropylethylamine, N-methylmorpholine or pyridine, or an inorganic base such as an alkali metal carbonate. The reaction is typically conducted at ambient temperature for 0.5 to 16 h, or until completion of the reaction has been achieved, as determined by chromatographic or spectroscopic methods. Reactions of sulfonyl halides with various primary and secondary amines are well known in the literature, and the variations of the conditions will be evident for those skilled in the art.

Sulfonylchlorides of formula (II) (wherein L¹ represents chlorine) are conveniently prepared by oxidative chlorination of compounds of formula (IV)

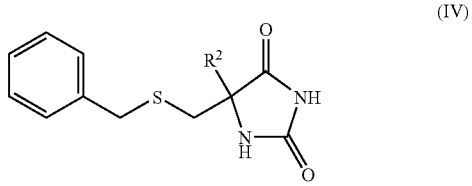

using methods that will be readily apparent to those skilled in the art (Mosher, J., *J. Org. Chem.* 1958. 23, 1257; Griffith, O., *J. Biol. Chem.* 1983. 258, (3), 1591; WO 02/074767).

Compounds of formula (III) can be prepared by various methods described in the literature or variations thereon as will be appreciated by those skilled in the art of synthetic organic chemistry. Suitable methods include, but are not limited to, those described below and are shown in Scheme 1.

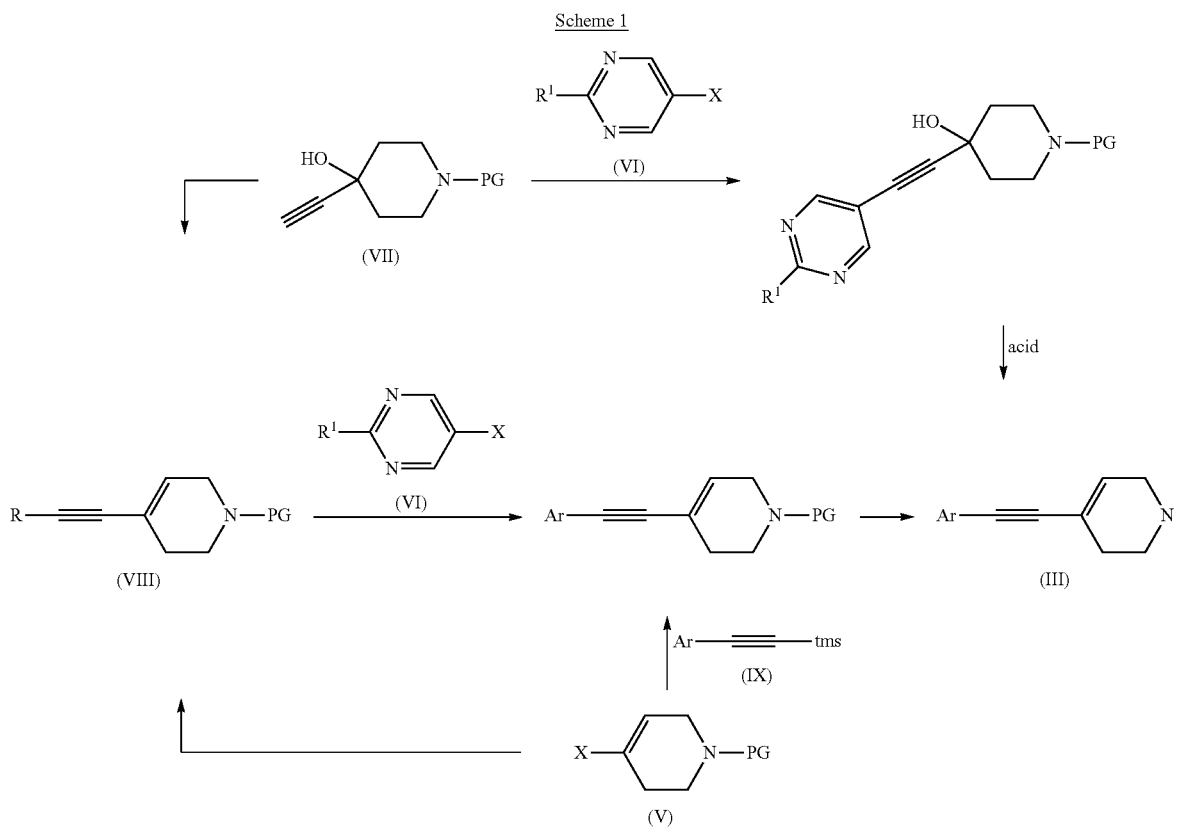

In Scheme 1, PG represents a suitable protecting group such as t-Boc; X represents a leaving group such as a halide or a triflate; R represents hydrogen or trimethylsilyl; tms represents trimethylsilyl; Ar represents a 5-pyrimidinyl ring substituted at the 2-position by $R^1$; and $R^1$ is as defined in formula (I).

The reaction between the aryl- or vinyl derivative [(V) or (VD] and an acetylene [(VII), (VIII) or (IX)] can be accomplished, optionally in a suitable solvent, using a catalyst such as a suitable palladium salt, for example, $PdCl_2(PPh_3)_2$, with/or without an added copper salt and with an amine base such as piperidine, triethylamine, diisopropylamine or diisopropylethylamine. When used, the added solvent may be, for example, tetrahydrofuran, acetonitrile or N,N-dimethylformamide. The reaction is conducted at ambient to reflux temperature for 20 minutes to several hours until chromatographic or spectroscopic methods indicate completion of the reaction. Palladium catalysed reactions involving acetylenic compounds are well known in the literature, and variations of the conditions will be evident for those skilled in the art. General methodology of this type is described in, for example, Brandsma, L., *Synthesis of Acetylenes, Allenes and Cumulenes: Methods and Techniques,* 2004, Elsiever Academic Press, chapter 16, pages 293-317; *Transition Metals-Catalysed Couplings of Acetylenes with $sp^2$-halides,* Sonogashira, K., *J. Organomet. Chem.,* 2002, 653, 46-49; Tykwinski, R. R., *Angew. Chem. Int. Ed.,* 2003, 42, 1566-1568.

The vinyl triflate (V) wherein X is O-triflate and PG is t-Boc can be prepared as described in the literature (Wustrow, D. J., *Synthesis,* 1991, 993-995).

Suitable substituted pyrimidinyl halides or triflates of formula (VI) can be prepared by various methods described in the literature, for example, Budesinsky, Z. et al., *Coll. Czech. Chem. Commun.,* 1949, 14, 223-235; Takahashi et al., *Chem. Pharm. Bull.,* 1958, 6, 334-337; U.S. Pat. No. 4,558,039.

The acetylenic compound (VIII) can be prepared from the triflate (V) via a palladium catalysed coupling reaction with trimethylsilylacetylene followed by, if necessary, deprotection of the trimethylsilyl group using, for example, potassium fluoride in a suitable solvent. Alternatively, preparation of compound (VIII) wherein R is H and PG is t-Boc can be accomplished by dehydrating a compound of formula (VII), for example, by mesylation followed by treatment with a suitable base, for example, diisopropylethylamine.

Acetylenic heteroaryl compounds of formula (IX) can be prepared by various methods described in the literature.

In process (b), the reactions are carried out using methods similar to those described above for the preparation of compounds of formula (VIII). If necessary, one nitrogen in the hydantoin ring of compounds of formula (X) can be protected using SEMCl ($R^3$=SEM) before the palladium catalysed reaction is performed. Compounds of formula (X) can be prepared by acid catalysed deprotection of compounds of formula (V) (PG=t-Boc), followed by reaction with a compound of formula (II), in the same way as described above to for the preparation of compounds of formula (I).

In process (c), the reactions are carried out in a similar manner to those described above for the preparation of compounds of formula (VIII). If necessary, one nitrogen of the hydantoin ring of compounds of formula (XI) can be protected using SEMCl ($R^3$=SEM) before the palladium catalysed reaction is performed. Compound (XI) is conveniently prepared from compound (VIII) wherein R is trimethylsilyl and PG is t-Boc by acid catalysed removal of the t-Boc group (for example, using acetyl chloride in methanol), followed by reaction with a compound of formula (II), as described above for the reaction between compounds of formulae (II) and (III).

It will be appreciated by those skilled in the art that in the processes of the present invention certain potentially reactive functional groups such as hydroxyl or amino groups in the starting reagents or intermediate compounds may need to be protected by suitable protecting groups. Thus, the preparation of the compounds of the invention may involve, at various stages, the addition and removal of one or more protecting groups.

Suitable protecting groups and details of processes for adding and removing such groups are described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).

The compounds of the invention and intermediates thereto may be isolated from their reaction mixtures and, if necessary further purified, by using standard techniques.

The present invention will now be further explained by reference to the following illustrative examples.

General Methods $^1$H NMR and $^{13}$C NMR spectra were recorded on a Varian Inova 400 MHz or a Varian to Mercury-VX 300 MHz instrument. The central peaks of chloroform-d ($\delta_H$ 7.27 ppm), dimethylsulfoxide-$d_6$ ($\delta_H$ 2.50 ppm), acetonitrile-$d_3$ ($\delta_H$ 1.95 ppm) or methanol-$d_4$ ($\delta_H$ 3.31 ppm) were used as internal references. Column chromatography was carried out using silica gel (0.040-0.063 mm, Merck). A Kromasil KR-100-5-$C_{18}$ column (250×20 mm, Akzo Nobel) and mixtures of acetonitrile/water with 0.1% TFA at a flow rate of 10 mL/min were used for preparative HPLC. Unless stated otherwise, starting materials were commercially available. All solvents and commercial reagents were of laboratory grade and were used as received.

The following method was used for LC/MS analysis:
Instrument Agilent 1100; Column Waters Symmetry 2.1×30 mm; Mass APCI; Flow rate 0.7 mL/min; Wavelength 254 or 220 nm; Solvent A: water+0.1% TFA; Solvent B: acetonitrile+0.1% TFA; Gradient 15-95%/B 2.7 min, 95% B 0.3 min.

The following method was used for LC analysis:
p Method A. Instrument Agilent 1100; Column: Kromasil C18 100×3 mm, 5µ particle size, Solvent A: 0.1% TFA/water, Solvent B: 0.08% TFA/acetonitrile Flow rate 1 mL/min, Gradient 10-100%/B 20 min, 100% B 1 min. Absorption was measured at 220, 254 and 280 nm.

Method B. Instrument Agilent 1100; Column: XTerra C 8, 100×3 mm, 5µ particle size, Solvent A: 15 mM $NH_3$/water, Solvent B: acetonitrile Flow rate 1 mL/min, Gradient 10-100%/B 20 min, 100% B 1 min. Absorption was measured at 220, 254 and 280 nm.

Abbreviations:
Ac acetyl
DMF N,N-dimethylformamide
DMSO dimethyl sulfoxide
eq. equivalent
Et ethyl
LDA lithium diisopropyl amide
Me methyl
MS mass spectroscopy
tert tertiary
THF tetrahydrofuran
TFA trifluoroacetic acid

EXAMPLE 1

(5S)-5-({[4-[(2-Cyclopropylpyrimidin-5-yl)ethynyl]-3,6-dihydropyridin-1(2H)-yl]sulfonyl}methyl)-5-methylimidazolidine-2,4-dione The title compound was prepared following the general method of Yamanaka et al, *Synth. Commun.*, 1983, 312-314. To 5-bromo-2-cyclopropylpyrimidine (110 mg, 0.55 mmol) and (5S)-5-({[(4-ethynyl-3,6-dihydropyridin-1(2H)-yl)sulfonyl]methyl}-5-methylimidazolidine-2,4-dione (180 mg, 0.61 mmol) in THF (3 mL) was added Et$_3$N (1 mL) and DMF (1 mL) at 35° C. After a solution was formed, CuI (4 mol %) and PdCl$_2$(PPh$_3$)$_2$ (2 mol %) were added and the mixture was heated at 72° C. for 6 hours. The mixture was partitioned between EtOAc (15 mL) and water (10 mL), and the aqueous layer was extracted three times with EtOAc. The combined organic layers were dried and concentrated to give the crude product as a yellow oil. The title compound (65 mg) was obtained by purification using preparative HPLC.

$^1$H-NMR (DMSO-d$_6$): δ 10.75 (1H, s); 8.72 (2H, s); 8.03 (1H, s); 6.28 (1H, m); 3.84 (2H, m); 3.47 (2H, q); 3.30 (2H, m); 2.37 (2H, m); 2.21 (1H, m); 1.33 (3H, s); 1.10 (2H, m); 1.02 (2H, m).

APCI-MS m/z: 416 [MH$^+$].

a) 5-Bromo-2-cyclopropylpyrimidine

5-Bromo-2-cyclopropylpyrimidine was prepared by the method of Budesinsky, Z., *Coll. Czech. Chem. Commun.*, 1949, 14, 223-235. Cyclopropanecarboximidamide hydrochloride (2.5 g, 20.7 mmol) was dissolved in EtOH (4 mL), freshly prepared 4.1M NaOEt in EtOH (4.8 mL) was added followed by mucobromic acid (2.7 g, 10.3 mmol). The mixture was heated to 56° C. for 30 minutes, more NaOEt in EtOH (4.1M, 3.2 mL) was added and the reaction was stirred at 56° C. for another 15 minutes and then at room temperature overnight. The solvent was evaporated off, aqueous HCl (2M, 10 mL) was added and the brown solid was filtered off. The aqueous layer was extracted three times with dichloromethane. The combined organic layers were dried and concentrated to give a brown oil that together with the solid gave crude intermediate 5-bromo-2-cyclopropylpyrimidine-4-carboxylic acid (1.6 g). The crude intermediate was heated at 140° C. for 8 minutes to give a brown sticky oil that was then partly dissolved in dichloromethane. The solution was decanted from the mixture and concentrated to give the subtitle compound as an oil (673 mg).

$^1$H-NMR (CDCl$_3$): δ 8.61 (2H, s); 2.25 (1H, m); 1.13 (4H, m).

APCI-MS m/z: 199/201 1:1 [MH$^+$].

b) (5S)-5-{[(4-Ethynyl-3,6-dihydropyridin-1(2H)-yl)sulfonyl]methyl}-5-methylimidazolidine-2,4-dione (5S)-5-Methyl-5-({[4-[(trimethylsilyl)ethynyl]-3,6-dihydropyridin-1(2H)-yl]sulfonyl}methyl)imidazolidine-2,4-dione (2.27 g, 6.0 mmol) and potassium fluoride (1.07 g, 18.4 mmol) were stirred overnight at room temperature in methanol (50 mL). The solvent was evaporated off, the residue dissolved in EtOAc, washed with water followed by brine, dried (sodium sulphate) and evaporated. The residue was purified by column chromatography eluting with iso-hexane/EtOAc 1:1 to give a solid product (1.81 g).

$^1$H NMR (CDCl$_3$) δ 1.66 (3H, s), 2.37 (2H, dt), 2.95 (1H, s), 3.24-3.50 (4H, m), 3.89 (2H, t), 6.11 (1H, s), 6.68 (1H, s), 8.75 (1H, s).

APCI-MS m/z: 298 [MH$^+$].

c) (5S)-5-Methyl-5-({[4-[(trimethylsilyl)ethynyl]-3,6-dihydropyridin-1(2H)-yl]sulfonyl}methyl)imidazolidine-2,4-dione 4-[(Trimethylsilyl)ethynyl]-1,2,3,6-tetrahydropyridine hydrochloride (3.43 g, 15.9 mmol) was stirred in THF (100 mL) with [(4S)-4-methyl-2,5-dioxoimidazolidin-4-yl]methanesulfonyl chloride (3.39 g, 15 mmol) and cooled in an ice salt bath (temperature about –10° C.). N-Ethyldiisopropylamine (5.13 mL, 30 mmol) in THF (100 mL) was added dropwise over 2 hours and the mixture stirred a further 2 hours. The reaction mixture was washed with water, the aqueous layer extracted into EtOAc (×2), the organic phases combined, washed with 2M HCl (×2), saturated bicarbonate solution (x2), followed by brine, dried (sodium sulphate) and evaporated to give the crude product (5.06 g). This was used without further purification.

$^1$H NMR (DMSO-d$_6$) δ 10.74 (1H, s), 8.01 (1H, s), 6.13 (1H, quintet), 3.75 (2H, d), 3.44 (2H, dd), 3.23 (2H, t), 2.18-2.28 (2H, m), 1.32 (3H, s), 1.32 (9H, s).

APCI-MS m/z: 370 [MH$^+$].

d) 4-[(Trimethylsilyl)ethynyl]-1,2,3,6-tetrahydropyridine hydrochloride tert-Butyl 4-[(trimethylsilyl)ethynyl]-3,6-dihydropyridine-1(2H)-carboxylate (2.75 g, 9.8 mmol) was stirred in methanol (10 mL) and acetyl chloride (2.1 mL, 29.2 mmol) was added dropwise. The temperature rose from 18° C. to 30° C. during the addition, and the mixture was kept at 40° C. until there was no more starting material by tlc. The mixture was cooled to room temperature, EtOAc (15 mL) was added and the solid filtered off to give an off-white solid (1.6 g).

$^1$H NMR (DMSO-d$_6$) δ 9.46 (2H, s), 6.09 (1H, quintet), 3.60 (2H, dd), 3.13 (2H, t), 2.35 (2H, td), 0.17 (8H, s).

APCI-MS m/z: 180 [MH$^+$].

e) tert-Butyl 4-[trimethylsilyl)ethynyl]-3,6-dihydropyridine-1(2H)-carboxylate Prepared from N-Boc-piperidin-4-one as in WO 96/05200.

$^1$H NMR (CDCl$_3$) δ 6.05 (1H, s), 3.94 (2H, dd), 3.47 (2H, t), 2.23 (2H, dq), 1.45 (10H), s), 0.15 (8H, s).

GCMS-MS m/z: 223 [M-55].

f) [(4S)-4-Methyl-2,5-dioxoimidazolidin-4-yl]methanesulfonyl chloride

Prepared according to methods described in the following publications: Mosher, J., *J. Org. Chem.* 1958. 23, 1257; Griffith, O., *J. Biol. Chem.* 1983. 258, (3), 1591; and WO 02/074767.

EXAMPLE 2

(5S)-5-Methyl-5-({[4-{2-(methylthio)pyrimidin-5-yl]ethynyl}-3,6-dihydropyridin-1(2H)-yl]sulfonyl}methyl)imidazolidine-2,4-dione The title compound was prepared by the general method described by Nishihara et al., *J. Org. Chem.*, 2000, 65, 1780-1787. To a solution of 2-(methylthio)-5-[(trimethylsilyl)ethynyl]pyrimidine (0.55 g, 2.47 mmol) and 1-{[(4-methyl-2,5-dioxoimidazolidin-4-yl)methyl]sulfonyl}-1,2,3,6-tetrahydropyridin-4-yl trifluoromethanesulfonate (0.94 g, 2.22 mmol) in DMF (5 mL) was added CuI (10 mol %) and PdCl$_2$(PPh$_3$)$_2$ (5 mol %) and the mixture was heated at 85° C. for 6 hours. The mixture was partitioned between EtOAc (20 mL) and water (10 mL), and the aqueous layer was extracted three times with EtOAc. The combined organic layers were washed with brine, water and concentrated to a brown oil (1.6 g). The title compound was obtained as a solid (10 mg) following purification by preparative HPLC (using a Xterra-Prep-MS-C18 (50×19) column with a 12 minutes gradient 5-35% of acetonitrile in water with 0.06% NH$_3$).

$^1$H-NMR (DMSO-d$_6$): δ 10.75 (1H, s); 8.73 (2H, s); 8.02 (1H, s); 6.29 (1H, m); 3.84 (2H, m); 3.48 (2H, q); 3.30 (2H, m); 2.53 (3H, s); 2.38 (2H, m); 1.33 (3H, s).

APCI-MS m/z: 422 [MH$^+$].

a) 5-Bromo-2-(methylthio)pyrimidine

The subtitle compound was prepared following a method by Takahashi et al., *Chem. Pharm. Bull.*, 1958, 6, 334-337. To a solution of 5-bromo-2-chloropyrimidine (1.0 g, 5.2 mmol) in EtOH was added sodium methanethiolate (0.36 g, 5.2 mmol) at room temperature and the reaction mixture was stirred overnight. The mixture was partitioned between EtOAc (15 mL) and water (10 mL). The aqueous layer was extracted twice with EtOAc and washed with brine. The combined organic layers were dried and concentrated to give the subtitle compound as a white solid (1.1 g).

$^1$H-NMR (CD$_3$OD): δ 8.66 (2H, s); 2.54 (3H, s).
APCI-MS m/z: 204/206 1:1 [MH$^+$].

b) 2-(Methylthio)-5-[(trimethylsilyl)ethynyl]pyrimidine

The subtitle compound was prepared following a method by Yamanaka et al, *Synth. Commun.*, 1983, 312-314. To 5-bromo-2-(methylthio)pyrimidine (0.60 g, 2.9 mmol) in Et$_3$N (3 mL) was added DMF (0.5 mL), CuI (5 mol %) and PdCl$_2$(PPh$_3$)$_2$ (3 mol %). The mixture was heated at 95° C. for 12 hours in a sealed tube and then partitioned between Et$_2$O (30 mL) and water (10 mL). The aqueous layer was extracted twice with Et$_2$O and the combined organic layers were washed with water, dried and concentrated to give the crude product as a brown oil. The compound was purified by flash chromatography using a gradient of 10-60% EtOAc in heptane, which gave the subtitle compound as a colourless oil (0.55 g).

$^1$H-NMR (CDCl$_3$): δ 8.56 (2H, s); 2.58 (3H, s); 0.27 (9H, s).
APCI-MS m/z: 223 [MH$^+$].

c) 1-({[(4S)-4-Methyl-2,5-dioxoimidazolidin-4-yl]methyl}sulfonyl)-1,2,3,6-tetrahydropyridin-4-yl trifluoromethanesulfonate 4-{[(Trifluoromethyl)sulfonyl]oxy}-1,2,3,6-tetrahydropyridinium chloride was reacted with [(4S)-4-methyl-2,5-dioxoimidazolidin-4-yl]methanesulfonyl chloride (Example 1f) in the same way as for Example 1c.

$^1$H NMR (DMSO-d$_6$) δ 10.77 (1H, s), 8.04 (1H, d), 6.10 (1H, t), 3.88 (2H, q), 3.36-3.58 (4H, m), 2.50-2.56 (2H, m), 1.32 (3H, s).

APCI-MS m/z: 422 [MH$^+$].

d) 4-{[(Trifluoromethyl)sulfonyl]oxy}-1,2,3,6-tetrahydropyridinium chloride tert-Butyl 4-{[(trifluoromethyl)sulfonyl]oxy}-3,6-dihydropyridine-1(2H)-carboxylate (3.77 g, 11.4 mmol) was mixed with THF (15 mL) and concentrated hydrochloric acid (15 mL). After 1 hour, the mixture was evaporated and dried by azeotropic evaporation with toluene and methanol to give a beige solid (88%) that could be used without further purification.

$^1$H NMR (CDCl$_3$) δ 9.72 (2H, s), 6.22 (1H, s), 3.75 (2H, q), 3.30 (2H, t), 2.65 (2H, td),
APCI-MS m/z: 232 [MH$^+$].

e) tert-Butyl 4-{[(trifluoromethyl)sulfonyl]oxy}-3,6-dihydropyridine-1(2H)-carboxylate A solution of N-boc-piperidin-4-one (10.14 g, 50 mmol) in THF (80 mL) was added to a cooled solution (−78° C.) of 2M LDA in THF (30 mL, 60 mmol, 1.2 eq.) and THF (80 mL) over approximately 30 minutes. After stirring a further 10 minutes, a solution of 1,1,1-trifluoro-N-phenyl-N-[(trifluoromethyl)sulfonyl]methanesulfonamide (20 g, 56 mmol, 1.1 eq.) in THF (80 mL) was added and the mixture was allowed to warm to room temperature. The solution was washed with water, the aqueous layer washed with EtOAc (×2), organic phases combined and washed with saturated ammonium chloride solution, brine, dried (sodium sulphate) and evaporated. The residue was filtered through neutral Alumina (200 g) eluting with n-heptane followed by n-heptane/EtOAc 9:1. After evaporation the showed some triflating agent still present but the crude product was used without further purification. Yield (13.17 g, 79.5%). (Wustrow, D. J., *Synthesis*, 1991, 993-995).

$^1$H NMR (CDCl$_3$) δ 5.77 (1H, s), 4.05 (2H, q), 3.64 (2H, t), 2.45 (2H, quintet), 1.48 (9H, s).
GCMS-MS m/z: 274 [M-57].

EXAMPLE 3

(5S)-5-Methyl-({[4-{[2-(trifluoromethyl)pyrimidin-5-yl]ethynyl}-3,6-dihydropyridin-1(2H)-yl]sulfonyl}methyl)imidazolidine-2,4-dione The title compound was prepared in 48% yield from 2-(trifluoromethyl)-5-[(trimethylsilyl)ethynyl]pyrimidine by the same method as described for Example 2. White solid from 95% EtOH, decomp. 240-245° C.

$^1$H NMR (DMSO-d$_6$) δ 10.8 (1H, br s), 9.16 (2H, s), 8.05 (1H, s), 6.42 (1H, m), 3.88 (2H, m), 3.56 (1H, d), 3.42 (1H, d), 3.32 (2H, m), 2.41 (2H, m) and 1.33 (3H, s).

APCI-MS m/z: 444 [MH$^+$].

a) 2-(Trifluoromethyl)-5-[(trimethylsilyl)ethynyl]pyrimidine 2-(Trifluoromethyl)pyrimidine-5-yl trifluoromethanesulfonate (0.45 g, 1.5 mmol) and dry triethylamine (1.0 mL) were mixed in a screw-cap vial. The solution was purged with dry argon for 10 minutes. Trimethylsilylacetylene (0.43 mL, 3.0 mmol), finely ground CuI (0.010 g, 0.05 mmol) and PdCl$_2$(PPh$_3$)$_2$ (0.020 g, 0.030 mmol) were added. The vial was sealed and heated in an aluminum block at 80° C. After stirring for 5 hours the volatiles were evaporated at room temperature (the product sublimes at 35-40° C./10 mbar). The black residue was taken up in EtOAc (20 mL) and concentrated with silica (about 5 to 10 g) to dryness. Flash chromatography on silica with EtOAc/heptane (1:30) afforded 2-(trifluoromethyl)-5-[(trimethylsilyl)ethynyl]pyrimidine as a white solid (0.35 g, 95%), m.p. 75.5-76.0° C.

$^1$H NMR (CDCl$_3$) δ 8.90 (2H, s) and 0.30 (9H, s).

APCI-MS m/z: 245 [MH$^+$].

b) 2-(Trifluoromethyl)pyrimidine-5-yl trifluoromethanesulfonate

Triflic anhydride (1.01 mL, 6.0 mmol) was added dropwise to a stirred mixture of 2-(trifluoromethyl)pyrimidin-5-ol (prepared according to U.S. Pat. No. 4,558,039) (0.82 g, 5.0 mmol), toluene (10 mL) and aqueous tripotassium phosphate (30% by weight, 10 mL) at ice-bath temperature (Frantz et al., *Organic Letters*, 2002, 4(26), 4717-4718). When the addition was complete the ice-bath was taken away and the solution was stirred at ambient temperature for 30 minutes. The clear phases were separated and the organic layer was washed with water, then brine. Drying of the organic phase over anhydrous sodium sulfate, filtration and concentration by rotary evaporation at room temperature afforded 2-(trifluoromethyl)-pyrimidine-5-yl trifluoromethanesulfonate as a colourless oil (1.38 g, 93%). B.p. 75-77° C. (10 mbar).

$^1$H NMR (CDCl$_3$) δ 8.90 (2H, s).

EXAMPLE 4

(5S)-5-Methyl-5-({[4-[(2-methylpyrimidin-5-yl) ethynyl]-3,6-dihydropyridin-1(2H) -yl] sulfonyl}methyl)imidazolidine-2,4-dione tert-Butyl 4-[(2-methylpyrimidin-5-yl)ethynyl]-3,6-dihydropyridine-1(2H)-carboxylate was treated with TFA in EtOH and after completion of the reaction the solvent was evaporated and the mixture was freeze dried. The residue was taken up in DMF (1.5 mL) and the mixture was cooled to 4° C. N-Ethyldiisopropylamine (2.2 eq.) was added and the mixture was stirred for 20 minutes before adding [(4S)-4-methyl-2,5-dioxoimidazolidin-4-yl]methanesulfonyl chloride (Example 1f) (1.1 eq.) in DMF (1 mL). The mixture was stirred for 10 min at 4° C. and then stirred for 2 h at room temperature before the solvent was evaporated. The product was purified by preparative HPLC to give the title compound (0.022 g, 30%).

$^1$H NMR (DMSO-d$_6$); 10.75 (1H, s); 8.80 (2H, s); 8.02 (1H, s); 7.80 (1H, m); 7.32 (1H, d, J=8.1 Hz); 6.24 (1H, s); 3.81 (2H, d, J=3.2 Hz); 3.34-3.21 (2H, m); 3.30 (3H, s); 2.75 (2H, q, J=20.8 Hz); 2.34 (2H, m); 1.29 (3H, s); 1.19 (3H, t, J=7.6 Hz).

APCI-MS m/z: 390 [MH$^+$].

a) 2-Methyl-5-[(trimethylsilyl)ethynyl]pyrimidine

5-Bromo-2-methyl-pyrimidine (prepared according to UK patent application GB 2 157 288) (0.2 g, 1.16 mmol), (trimethylsilyl)acetylene (164 μL, 1.3 mmol), CuI (0.022 g, 0.116 mmol) and PdCl$_2$(PPh$_3$)$_2$ (0.082 g, 0.116 mmol) in Et$_3$N (2 mL) and THF (2 mL) were stirred at 80° C. for 4 h. After cooling, the solvents were removed under vacuum and the residue chromatographed to give the subtitle compound (0.16 g, 50%).

APCI-MS m/z: 191 [MH$^+$].

b) tert-Butyl 4-[(2-methylpyrimidin-5-yl)ethynyl]-3, 6-dihydropyridine-1(2H) -carboxylate To a solution of CuCl (1 mg, 0.01 mmol) and PdCl$_2$(PPh$_3$)$_2$ (0.003 g, 0.004 mmol) in DMF (2 mL) were added 2-methyl-5-[(trimethylsilyl)ethynyl]pyrimidine (0.088 g, 0.462 mmol) and tert-butyl 4-{[(trifluoromethyl)sulfonyl]oxy}-3,6-dihydropyridine-1(2H)-carboxylate (Example 2e) (0.183 g, 0.555 mmol) at room temperature. The reaction mixture was stirred for 8 h at 80° C. After cooling, the mixture was quenched with 1N HCl and extracted with ether (3x). The combined organic layers were washed with saturated aqueous NaHCO$_3$ solution, brine and dried. Filtration and evaporation afforded a brown oil, which was purified on HPLC to give the subtitle compound (0.062 g, 45%).

APCI-MS m/z: 300 [MH$^+$].

EXAMPLE 5

(5S)-5-({[4-[(2-Ethylpyrimidin-5-yl)ethynyl]-3,6-dihydropyridin-1(2H) -yl]sulfonyl}methyl)-5-methylimidazolidine-2,4-dione trifluoroacetate The title compound was made in the same way as described for Example 4. The 5-bromo- 2-ethyl-pyrimidine starting material was prepared using the methodology of GB 2 157 288.

$^1$H NMR (DMSO-d$_6$); 10.75 (1H, s); 8.82 (2H, s); 8.05 (1H, s); 6.24 (1H, s); 3.81 (2H, d, J=3.2 Hz); 3.34-3.21 (2H, m); 3.30 (3H, s); 2.92 (2H, q, J=17.8 Hz); 2.75 (2H, q, J=20.8 Hz); 2.34 (2H, m); 1.26 (3H, t, J=12.8 Hz); 1.19 (1H, s).

APCI-MS m/z: 404 [MH$^+$].

EXAMPLE 6

(5S)-5-({[4-[(2-Methoxypyrimidin-5-yl)ethynyl]-3, 6-dihydropyridin-1(2H) -yl]sulfonyl}methyl)-5-methylimidazolidine-2,4-dione The title compound was prepared from 5-bromo-2-methoxypyrimidine and (5S) -5-{[(4-ethynyl-3,6-dihydropyridin-1(2H)-yl)sulfonyl]methyl}-5-methylimidazolidine-2,4-dione in the same way as described in Example 1.

$^1$H NMR (DMSO-d$_6$): δ 10.75 (1H, s); 8.73 (2H, s); 8.04 (1H, s); 6.26 (1H, s); 3.95 (3H, s); 3.81 (2H, d, J=3.2 Hz); 3.34-3.21 (2H, m); 3.30 (3H, s); 2.75 (2H, q, J=20.8 Hz); 2.34 (2H, m); 1.19 (3H, t, J=7.6 Hz).

APCI-MS m/z: 406 [MH$^+$].

PHARMACOLOGICAL EXAMPLE

Isolated Enzyme Assays
MMP12

Recombinant human MMP 12 catalytic domain may be expressed and purified as described by Parkar A. A. et al, (2000), Protein Expression and Purification, 20, 152. The purified enzyme can be used to monitor inhibitors of activity as follows: MMP12 (50 ng/ml final concentration) is incubated for 60 minutes at room temperature with the synthetic substrate Mca-Pro-Cha-Gly-Nva-His-Ala-Dpa-NH$_2$ (10 μM) in assay buffer (0.1M "Tris-HCP" (trade mark) buffer, pH 7.3 containing 0.1M NaCl, 20 mM CaCl$_2$, 0.020 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:

% Inhibition is equal to the [Fluorescence$_{plus\ inhibitor}$−Fluorescence$_{background}$] divided by the [Fluorescence$_{minus\ inhibitor}$−Fluorescence$_{background}$].

MMP8

Purified pro-MMP8 is purchased from Calbiochem. The enzyme (at 10 μg/ml) is activated by p-amino-phenyl-mercuric acetate (APMA) at 1 mM for 2.5 h, 35° C. The activated enzyme can be used to monitor inhibitors of activity as follows: MMP8 (200 ng/ml final concentration) is incubated for 90 minutes at 35° C. (80% H₂O) with the synthetic substrate Mca-Pro-Cha-Gly-Nva-His-Ala-Dpa-NH₂ (12.5 µM) in assay buffer (0.1M "Tris-HCl" (trade mark) buffer, pH 7.5 containing 0.1M NaCl, 30 mM CaCl₂, 0.040 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:

% Inhibition is equal to the [Fluorescence$_{plus\ inhibitor}$–Fluorescence$_{background}$] divided by the [Fluorescence$_{minus\ inhibitor}$–Fluorescence$_{background}$].

MMP9

Recombinant human MMP9 catalytic domain was expressed and then purified by Zn chelate column chromatography followed by hydroxamate affinity column chromatography. The enzyme can be used to monitor inhibitors of activity as follows: MMP9 (5 ng/ml final concentration) is incubated for 30 minutes at RT with the synthetic substrate Mca-Pro-Cha-Gly-Nva-His-Ala-Dpa-NH₂ (5 µM) in assay buffer (0.1 M "Tris-HCl" (trade mark) buffer, pH 7.3 containing 0.1M NaCl, 20 mM CaCl₂, 0.020 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:

% Inhibition is equal to the [Fluorescence$_{plus\ inhibitor}$–Fluorescence$_{background}$] divided by the [Fluorescence$_{minus\ inhibitor}$–Fluorescence$_{background}$].

MMP14

Recombinant human MMP 14 catalytic domain may be expressed and purified as described by Parkar A. A. et al, (2000), Protein Expression and Purification, 20, 152. The purified enzyme can be used to monitor inhibitors of activity as follows: MMP14 (10 ng/ml final concentration) is incubated for 60 minutes at room temperature with the synthetic substrate Mca-Pro-Cha-Gly-Nva-His-Ala-Dpa-NH₂ (10 µM) in assay buffer (0.1M "Tris-HCl" (trade mark) buffer, pH 7.5 containing 0.1M NaCl, 20 mM CaCl₂, 0.020 mM ZnCl and 0.05% (w/v) "Brij 35" (trade mark) detergent) in the presence (5 concentrations) or absence of inhibitors. Activity is determined by measuring the fluorescence at λex 320 nm and λem 405 nm. Percent inhibition is calculated as follows: % Inhibition is equal to the [Fluorescence$_{plus\ inhibitor}$–Fluorescence$_{background}$] divided by the [Fluorescence$_{minus\ inhibitor}$–Fluorescence$_{background}$].

A protocol for testing against other matrix metalloproteinases, including MMP9, using expressed and purified pro MMP is described, for instance, by C. Graham Knight et al., (1992) FEBS Lett., 296(3), 263-266.

MMP19

Recombinant human MMP19 catalytic domain may be expressed and purified as described by Parkar A. A. et al, (2000), Protein Expression and Purification, 20:152. The purified enzyme can be used to monitor inhibitors of activity as follows: MMP19 (40 ng/ml final concentration) is incubated for 120 minutes at 35° C. with the synthetic substrate Mca-Pro-Leu-Ala-Nva-Dpa-Ala-Arg-NH₂ (5 µM) in assay buffer (0.1M "Tris-HCl " (trade mark) buffer, pH 7.3 containing 0.1M NaCl, 20 mM CaCl₂, 0.020 mM ZnCl and 0.05% (w/v) "Brij 35" (trade mark) detergent) in the presence (5 concentrations) or absence of inhibitors. Activity is determined by measuring the fluorescence at λex 320 nm and λem 405 nm. Percent inhibition is calculated as follows: % Inhibition is equal to the [Fluorescence$_{plus\ inhibitor}$–Fluorescence$_{background}$] divided by the [Fluorescence$_{minus\ inhibitor}$–Fluorescence$_{background}$].

Protein Binding

Plasma protein binding was determined by ultrafiltration in an automated 96 well format assay. On each test occasion the plasma protein binding of a reference compound (budesonide) was monitored in parallel.

Test compounds (10 mM dissolved in DMSO) were added to plasma to a final concentration of 10 µM and equilibrated at room temperature for 10 minutes. 350 µL of the plasma was transferred to an ultrafiltration plate, Microcon-96 (10 kDa cutoff, Millipore). The ultrafiltration plate was centrifuged at 3000 G for 70 minutes at room temperature. After centrifugation, the concentration of the compounds in the obtained plasma water (the unbound fraction) was determined by LC-MS/MS using a 3-point calibration curve and compared to the concentration in the original spiked plasma.

The analyses were performed using a gradient chromatographic system with acetic acid/acetonitrile as mobile phases. The detection was done using a triple quadropole mass spectrometer, API3000 or API4000, from Applied Biosystems, with an electrospray interface.

Protocol for Determination of Solubility

The solubility of test compounds in 0.1M phosphate buffer, pH 7.4, was determined as follows:

The test compound (1 mg) was weighed into a 2 mL glass vial with a screw cap and 0.1 M phosphate buffer pH 7.4. (1.00 mL) was added. The sample vial was then sonicated for about 10 minutes and then placed on a shake board overnight at 20° C. The contents of the sample vial were then filtered through a Millipore Millex-LH 0.45 µm filter into a new 2 mL glass vial to give a clear solution. The clear solution (40 µL) was transferred to a new 2 mL glass vial and diluted with 0.1 M phosphate buffer, pH 7.4 (960 µL).

A standard calibration curve for each particular test compound was established using solutions of known concentration. These solutions of known concentration were normally chosen to have concentrations of ~10 µg/mL and ~50 µg/mL. They were prepared by dissolving a known weight of the compound in 99.5% ethanol (500 µL) and then sonicating for one minute if necessary. If the compound was still not completely dissolved, DMSO (500 µL) was added and the mixture sonicated for an additional one minute. The resulting solution was then diluted to the appropriate volume with a mixture of acetonitrile/100 mM ammonium acetate pH 5.5 20-50/80-50. If necessary, a further, more dilute, standard solution was prepared by dilution.

Test compound solutions and standard solutions were then analysed by HPLC with UV-detection using the following parameters and the solubility of the test compound in 0.1M phosphate buffer was thereby determined:

| | |
|---|---|
| HPLC-equipment: | HP1100/HP1050 |
| Column: | HyPURITY Advanced, 5 µm, 125 × 3 mm |
| Column temperature: | RT |
| Flow rate: | 1 mL/min |
| Mobile phase: | A = acetonitrile |
| | B = 100 mM ammonium acetate pH 5.5 |
| Isocratic ratio: | A/B 20-50/80-50 |
| UV detector: | 254 nm (220-280 nm) |
| Injection volume: | 20 µL |
| Chromatographic data handling system: | ATLAS/Xchrome |

Protocol for Determination of Log D

Log D values at pH 7.4 were determined using a shake flask method. An appropriate small amount of the test compound was placed in a 2 mL glass vial with a screw cap at room temperature and 600 μL of 1-octanol (saturated with 10 mM phosphate buffer pH 7.4) was added. The vial was then sonicated for one minute so as to dissolve the compound completely. Then 600 μL of 10 mM phosphate buffer pH 7.4 (saturated with 1-octanol) was added and the vial was shaken for 4 minutes to mix the two phases. The two phases were then separated by centrifugation of the sample at 1000 g for 10 minutes at room temperature. Finally, the separated aqueous and organic phases were analysed in duplicate by HPLC using the following conditions:

| Injector: | Spark Holland, Endurance |
|---|---|
| Pump: | HP1050 |

| | |
|---|---|
| Detector: | Kratos, Spectroflow 783 |
| Column: | YMC Pro C18, 5 μm, 50 × 4 mm, Part no. AS12S050504QT |
| Column temperature: | RT |
| Flow rate: | 1 mL/min |
| Mobile phase: | A = acetonitrile<br>B = 25 mM formic acid<br>C = 100 mM ammonium acetate pH 5.5<br>D = 0.05% ammonium acetate |
| Gradient: | 0.00 min A/B or A/C or A/D 5/95<br>5.00 min A/B or A/C or A/D 100/0<br>7.00 min A/B or A/C or A/D 100/0<br>7.02 min A/B or A/C or A/D 5/95 |
| UV detector: | 254 nm |
| Injection volume: | 50 μL of undiluted aqueous phase and 5 μL of 10 times diluted (with methanol) organic phase |
| Injection cycle time: | 11 min |
| Centrifuge: | Hettich, Universal 30RF |
| Vortex: | Scientific Industries, Vortex-2 genie |
| Chromatographic data handling system: | ATLAS/Xchrome |

The log $D_{pH7.4}$ value was automatically calculated (see equation below) by an Excel sheet after manual typing of compound peak area responses which were reported from the ATLAS chromatographic data handling system.

Calculation of log $D_{pH\,7.4}$ by equation:

$$\text{Log}\,D = \left(\frac{[Analyte]_{org}}{[Analyte]_{aq}}\right) = \log\left(\frac{Area_{org} \times \text{Dilution}\,factor_{org}}{Area_{aq} \times \text{Dilution}\,factor_{aq} \times \frac{V_{inj}(org)}{V_{inj}(aq)}}\right)$$

The following table shows data for a representative selection of the compounds of the present invention and for selected compounds from WO 02/074767.

TABLE

| Compound | hMMP12 IC$_{50}$ (nM) | hMMP9 IC$_{50}$ (nM) | hMMP8 IC$_{50}$ (nM) | hMMP14 IC$_{50}$ (nM) | hMMP19 IC$_{50}$ (nM) | Solubility pH 7.4 (μM) | Protein binding (% free) |
|---|---|---|---|---|---|---|---|
| Example 5 | 9 | 9 | 1,140 | >10,000 | >10,000 | 91 | 47 |
| Example 3 | 6 | 5 | 547 | >10,000 | 7,900 | 118 | 33 |
| Example 1 | 6 | 5 | 2,530 | >10,000 | >10,000 | 396 | 18 |
| WO 02/074767, page 120 (5S)-5-({[4-[(4-chlorophenyl)ethynyl]-3,6-dihydropyridin-1(2H)-yl]sulfonyl}-methyl)-5-methyl-imidazolidine-2,4-dione | 2 | 9 | 180 | 4,300 | 3,980 | 49 | 1.75 |
| WO 02/074767, page 120 (5S)-5-methyl-5-({[4-[(4-methylphenyl)ethynyl]-3,6-dihydropyridin-1(2H)-yl]sulfonyl}-methyl)imidazolidine-2,4-dione | 3 | 34 | 384 | 4,430 | 1,970 | 72 | 2.25 |

The invention claimed is:

1. A compound selected from the group consisting of:
   (5S)-5-methyl-5-({[4-{[2-(methylthio)pyrimidin-5-yl]ethynyl}-3,6-dihydropyridin-1(2H)-yl]sulfonyl}methyl)imidazolidine-2,4-dione;
   (5S)-5-methyl-5-({[4-{[2-(trifluoromethyl)pyrimidin-5-yl]ethynyl}-3,6-dihydropyridin-1(2H)-yl]sulfonyl}methyl)imidazolidine-2,4-dione;
   (5S)-5-methyl-5-({[4-[(2-methylpyrimidin-5-yl)ethynyl]-3,6-dihydropyridin-1(2H)-yl]sulfonyl}methyl)imidazolidine-2,4-dione;
   (5S)-5-({[4-[(2-ethylpyrimidin-5-yl)ethynyl]-3,6-dihydropyridin-1(2H)-yl]sulfonyl}methyl)-5-methylimidazolidine-2,4-dione; and
   (5S)-5-({[4-[(2-methoxypyrimidin-5-yl)ethynyl]-3,6-dihydropyridin-1(2H)-yl]sulfonyl}methyl)-5-methylimidazolidine-2,4-dione;
   and pharmaceutically acceptable salts thereof.

2. A pharmaceutical composition comprising a compound of formula (I) or a pharmaceutically acceptable salt thereof as claimed in claim 1 in association with a pharmaceutically acceptable adjuvant, diluent or carrier.

* * * * *